United States Patent
Yoshida et al.

(10) Patent No.: US 9,494,549 B2
(45) Date of Patent: Nov. 15, 2016

(54) GAS SENSOR CONTROL APPARATUS AND GAS SENSOR SYSTEM

(71) Applicant: NGK SPARK PLUG CO., LTD., Nagoya-shi, Aichi (JP)

(72) Inventors: Akihiro Yoshida, Ichinomiya (JP); Kenji Kato, Nagoya (JP); Koji Shiotani, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 352 days.

(21) Appl. No.: 14/188,981

(22) Filed: Feb. 25, 2014

(65) Prior Publication Data

US 2014/0238853 A1  Aug. 28, 2014

(30) Foreign Application Priority Data

Feb. 27, 2013 (JP) .................... 2013-036939

(51) Int. Cl.
| | |
|---|---|
| G01N 27/409 | (2006.01) |
| G01N 27/406 | (2006.01) |
| G01N 27/416 | (2006.01) |
| G01N 33/00 | (2006.01) |

(52) U.S. Cl.
CPC ........ G01N 27/409 (2013.01); G01N 27/4065 (2013.01); G01N 33/0037 (2013.01)

(58) Field of Classification Search
CPC ........... G01N 27/409; G01N 27/4065; G01N 33/0037
See application file for complete search history.

(56) References Cited

U.S. PATENT DOCUMENTS

| | | |
|---|---|---|
| 5,733,436 A | 3/1998 | Demisch et al. |
| 8,394,248 B2 | 3/2013 | Kobayashi et al. |
| 2001/0023823 A1 | 9/2001 | Takahashi et al. |
| 2009/0164091 A1 | 6/2009 | Kobayashi et al. |

FOREIGN PATENT DOCUMENTS

| | | |
|---|---|---|
| JP | 61-241647 A | 10/1986 |
| JP | 8-271470 A | 10/1996 |
| JP | 2001-318075 A | 11/2001 |
| JP | 2008-8668 A | 1/2008 |
| JP | 2009-168798 A | 7/2009 |

OTHER PUBLICATIONS

Oya et al. JP2008008668A , Jan. 17, 2008, English machine translation.*
Office Action dated Jun. 16, 2015, issued by the Japanese Intellectual Property Office in counterpart Japanese Application No. 2013-036939.

* cited by examiner

*Primary Examiner* — Susan D Leong
(74) *Attorney, Agent, or Firm* — Sughrue Mion, PLLC

(57) ABSTRACT

A gas sensor control apparatus for controlling a gas sensor element, the gas sensor element including first and second measuring chambers and the gas sensor control apparatus including first chamber control unit for controlling an oxygen concentration in the first chamber; second chamber control unit for applying a second chamber pump voltage to disassociate an oxygen-containing specific gas contained in the second chamber and thereby generate a concentration-dependent current; current detecting unit; voltage changing unit for changing the second chamber pump voltage; and deterioration determination unit for determining the deterioration state of the gas sensor element based on a transient response of the concentration-dependent current.

6 Claims, 7 Drawing Sheets

GAS SENSOR CONTROL APPARATUS AND GAS SENSOR SYSTEM

BACKGROUND OF THE INVENTION

1. Field of the Invention

The present invention relates to a gas sensor control apparatus and a gas sensor system for controlling a gas sensor element which detects a concentration of a specific gas.

2. Description of the Related Art

Conventionally, gas sensors are known which include a gas sensor element for detecting a concentration of a specific gas contained in exhaust emissions from an internal combustion engine, and a gas sensor control apparatus for controlling the gas sensor element. For example, Patent Literature 1 discloses a NOx sensor which includes a gas sensor element (a NOx sensor element) for detecting nitrogen oxides (NOx) as a specific gas, and a gas sensor control apparatus for controlling the gas sensor element so as to calculate a concentration of nitrogen oxides in a gas to be measured.

The NOx sensor element used for this purpose has a first measuring chamber and a second measuring chamber in an interior thereof, and includes a first pump cell and a second pump cell which are made of a solid electrolyte.

A gas to be measured is introduced into the first measuring chamber, and the first pump cell controls the gas contained in the first chamber gas to a predetermined oxygen concentration. The second chamber pump cell applies a predetermined second chamber pump voltage between a second chamber electrode which faces an interior of the second measuring chamber and a reference electrode which is exposed to an atmosphere of a reference oxygen concentration, to thereby dissociate an oxygen-containing specific gas contained in the second measuring chamber. In this manner, a current which corresponds to the concentration of the oxygen-containing specific gas in the second chamber gas flows between the second chamber electrode and the reference electrode. This enables the gas sensor control apparatus to detect a concentration of nitrogen oxides as a concentration of a specific gas based on the magnitude of the current.

[Patent Literature 1] JP-A-2009-168798

Problems to be Solved by the Invention

The response of the gas sensor element which is used in the gas sensor described above is known to exhibit delay as the sensor deteriorates with use. For example, a particularly highly accurate detecting performance is required of a NOx sensor which detects nitrogen oxides in the exhaust gas of a vehicle to meet recent severe NOx restrictions. However, in the event that the response of the NOx sensor is delayed as a result of the deterioration of a NOx sensor element which is part of the sensor, there is a concern that the required detecting performance can no longer be satisfied. To address this problem, the gas sensor control apparatus which controls the gas sensor element is required to properly determine the deterioration response of the gas sensor element having a delayed response.

SUMMARY OF THE INVENTION

The present invention has been made in view of the above problems of the prior art, and an object thereof is to provide a gas sensor control apparatus and a gas sensor system which can properly determine the deterioration state of a gas sensor element.

The above object has been achieved, in accordance with a first aspect of the invention, by providing (1) a gas sensor control apparatus for controlling a gas sensor element, the gas sensor element including: a first measuring chamber into which an external gas to be measured is introduced and a second measuring chamber in communication with the first measuring chamber and into which a first chamber gas in an interior of the first measuring chamber is introduced, the first measuring chamber and the second measuring chamber being formed in an interior of the gas sensor element; a second chamber pump cell made of a solid electrolyte; and a pair of electrodes which are provided on the second chamber pump cell and which are disposed inside and outside the second measuring chamber, the gas sensor control apparatus including: first chamber control unit for controlling an oxygen concentration of the first chamber gas in the interior of the first measuring chamber to a first concentration; second chamber control unit for applying a second chamber pump voltage and dissociating an oxygen-containing specific gas, which is contained in a second chamber gas in an interior of the second measuring chamber, between the pair of electrodes, so as to cause a concentration-dependent current, which corresponds to a concentration of the oxygen-containing specific gas in the second chamber gas in the interior of the second measuring chamber, to flow between the pair of electrodes; current detecting unit for detecting a magnitude of the concentration-dependent current which flows between the pair of electrodes; voltage changing unit for changing the second chamber pump voltage; and deterioration determination unit for determining the deterioration state of the gas sensor element based on a transient response of the concentration-dependent current which is generated in association with a change in the second chamber pump voltage.

The gas sensor control apparatus includes the voltage changing unit which changes the second chamber pump voltage applied between the pair of electrodes which are provided on the second chamber pump cell and the deterioration determination unit which determines the deterioration of the gas sensor element based on the transient response of the concentration-dependent current which is generated in association with the change in the second chamber pump voltage.

The present inventors found out that the transient response of the concentration-dependent current generated by changing the second chamber pump voltage differs depending upon the degree of deterioration of the gas sensor. Specifically, for example, suppose that the second chamber pump voltage is stepwise switched from the voltage which detects the specific gas concentration to a voltage which is higher than the detecting voltage in the stepwise state. Then, a transient response is generated in which the concentration-dependent current steeply rises immediately after the second chamber pump voltage has been so switched and then begins to decline (decay) after passing its peak.

In this case, the greater the extent to which the gas sensor element is deteriorated, the higher the peak value of the concentration-dependent current, and the slower (more moderate) the ensuing concentration-dependent current decline. Consequently, in this apparatus, it is possible to appropriately determine by the deterioration determination unit the deterioration state of the gas sensor element based on the transient response of the concentration-dependent current.

In addition, the way in which the second chamber pump voltage is changed by the voltage changing unit is not particularly limited, as long as a difference in the transient response of the concentration-dependent current can be appropriately obtained depending on the deterioration state of the gas sensor element. For example, a case is considered in which the second chamber pump voltage is switched in a stepwise manner to a higher voltage as described above, or oppositely to a low voltage. Additionally, the second chamber pump voltage may be changed in a ramp manner between the two voltage values. In addition, the second chamber pump voltage may be changed in a sine wave-like fashion over half a period, one period or several periods.

In addition, in determining the deterioration state of the gas sensor, any portion of the transient response of the concentration-representing current which is generated in association with the change in the second chamber pump voltage may be used, as long as the selected portion changes according to the deterioration state of the gas sensor. For example, when the second chamber pump voltage is switched in a stepwise state as described above, the deterioration state may be determined based on the peak value of the concentration-dependent current. Alternatively, the deterioration state may be determined based on the difference in decline pattern in the decline period of the concentration-dependent current. As a method for detecting the difference in decline pattern of the concentration-dependent current, a time constant of the change, a timing at which the concentration-dependent current becomes a predetermined value, a magnitude of the concentration-dependent current at a predetermined time or the like can be used for determining the deterioration state. Additionally, the deterioration state of the gas sensor may be determined by the use of two or more parameters including the peak value, the time constant of the decline and the like.

In a preferred embodiment (2) of the above gas sensor control apparatus (1), the voltage changing unit includes voltage switching unit for switching, in a stepwise state, the second chamber pump voltage from a detecting voltage for detecting a specific gas concentration to a determination voltage which is higher than the detecting voltage, and the deterioration determination unit determines the deterioration state of the gas sensor element based on, as the transient response of the concentration-representing current which is generated by the switching of the second chamber pump voltage by the voltage switching unit, a change in the concentration-dependent current during a decline period, which is a period after the concentration-dependent current rises to its peak from a pre-switching current before the switching of the second chamber pump voltage and then shifts to start declining.

When the second chamber pump voltage is switched from the detecting voltage to the determination voltage which is higher than the detecting voltage in a stepwise state by the voltage switching unit, as described above, a transient response is generated in which the concentration-dependent current steeply rises immediately after the switching of the second chamber pump voltage and then begins to decline after passing its peak. Then, this transient response is such that, as the gas sensor element further deteriorates, the peak value of the concentration-dependent current becomes greater and the concentration-dependent current declines at a slower rate in the ensuing decline. Consequently, the decline of the concentration-dependent current generated in the decline period by the switching of the second chamber pump voltage, that is, the change in the concentration-dependent current during the decline period, represents the extent to which the gas sensor element has deteriorated.

Because of this, in the gas sensor control apparatus (2), it is possible to appropriately determine the deterioration state of the gas sensor element based on the change in the concentration-dependent current during the decline period.

Specific methods for determining the deterioration state of the gas sensor element based on the change in the concentration-dependent current during the decline period include, for example, a method in which a timing is obtained at which the concentration-dependent current becomes a predetermined value, so that the timing thus obtained is used for making the determination, or a method in which a magnitude of the concentration-representing current obtained at a predetermined timing is used for making the determination.

In addition, the concentration-dependent current may be measured sequentially during the decline period to obtain a time constant for the decline, or a function parameter of a curve which matches the decline is obtained, so that the time constant or the function parameter thus obtained is used for making the determination.

In a preferred embodiment (3) of the above gas sensor control apparatus (2), the deterioration determination unit includes: timing detecting unit for detecting a threshold arrival timing at which a difference value between the concentration-dependent current and the pre-switching current becomes equal to or smaller than a predetermined first threshold current value during the decline period; and first determination unit for determining the deterioration state of the gas sensor element based on the threshold arrival timing.

In the above gas sensor control apparatus (3), the deterioration determination unit includes the timing detecting unit and the first determination unit, and the deterioration of the gas sensor element is determined based on the threshold arrival timing at which the difference value between the concentration-dependent current and the pre-switching current becomes equal to or smaller than the predetermined first threshold current value during the decline period.

By adopting this method, it is possible to appropriately determine the difference in change in the concentration-dependent current occurring during the decline period according to the extent of deterioration of the gas sensor element, based on the threshold arrival timing.

In a preferred embodiment (4) of the above gas sensor control apparatus (3), the first determination unit determines that the gas sensor element is deteriorated when a required time spent from the switching of the second chamber pump voltage to the threshold arrival timing is longer than a predetermined deterioration determination time length.

In the gas sensor control apparatus (4), it is possible to simply and appropriately determine whether or not the gas sensor element is deteriorated by comparing the required time from the switching of the second chamber pump voltage to the threshold arrival timing with the deterioration determination time length.

In a preferred embodiment (5) of the above gas sensor control apparatus (2), the deterioration determination unit includes: determination difference value obtaining unit for obtaining a determination difference value, which is a difference value between the concentration-dependent current at a predetermined deterioration determination time during the decline period and the pre-switching current; and second determination unit for determining the deterioration state of the gas sensor element based on the determination difference value.

In the gas sensor control apparatus (5), the deterioration determination unit includes the determination difference value obtaining unit and the second determination unit, and the deterioration state of the gas sensor element is determined based on the determination difference value which is the difference value between the concentration-dependent current at the predetermined deterioration determination time during the decline period and the pre-switching current.

By doing so, the difference in change in the concentration-dependent current during the decline period based on the deterioration of the gas sensor element is obtained as the difference in the determination difference value, so that it is possible to appropriately determine the deterioration state of the gas sensor. In addition, the time required for determining the deterioration state is determined by the predetermined deterioration determination time. Therefore, even though the concentration-dependent current declines moderately with progressing deterioration of the gas sensor element, there is no situation in which the time taken for determining the deterioration state of the gas sensor element is extended.

In a preferred embodiment (6) of the above gas sensor control apparatus (5), the second determination unit determines that the gas sensor element is deteriorated when the determination difference value is larger than a predetermined second threshold current value.

In the gas sensor control apparatus (6), it is possible to simply and appropriately determine the deterioration state of the gas sensor element by comparing the determination difference value with the predetermined second threshold current value.

In addition, according to a further aspect (7), the present invention provides a gas sensor system which comprises any of the gas sensor control apparatuses (1) to (7) above and a gas sensor including the gas sensor element. This gas sensor system makes it possible to provide a gas sensor system which can appropriately determine the deterioration state of the gas sensor element.

DESCRIPTION OF REFERENCE NUMERALS

Figure 1:
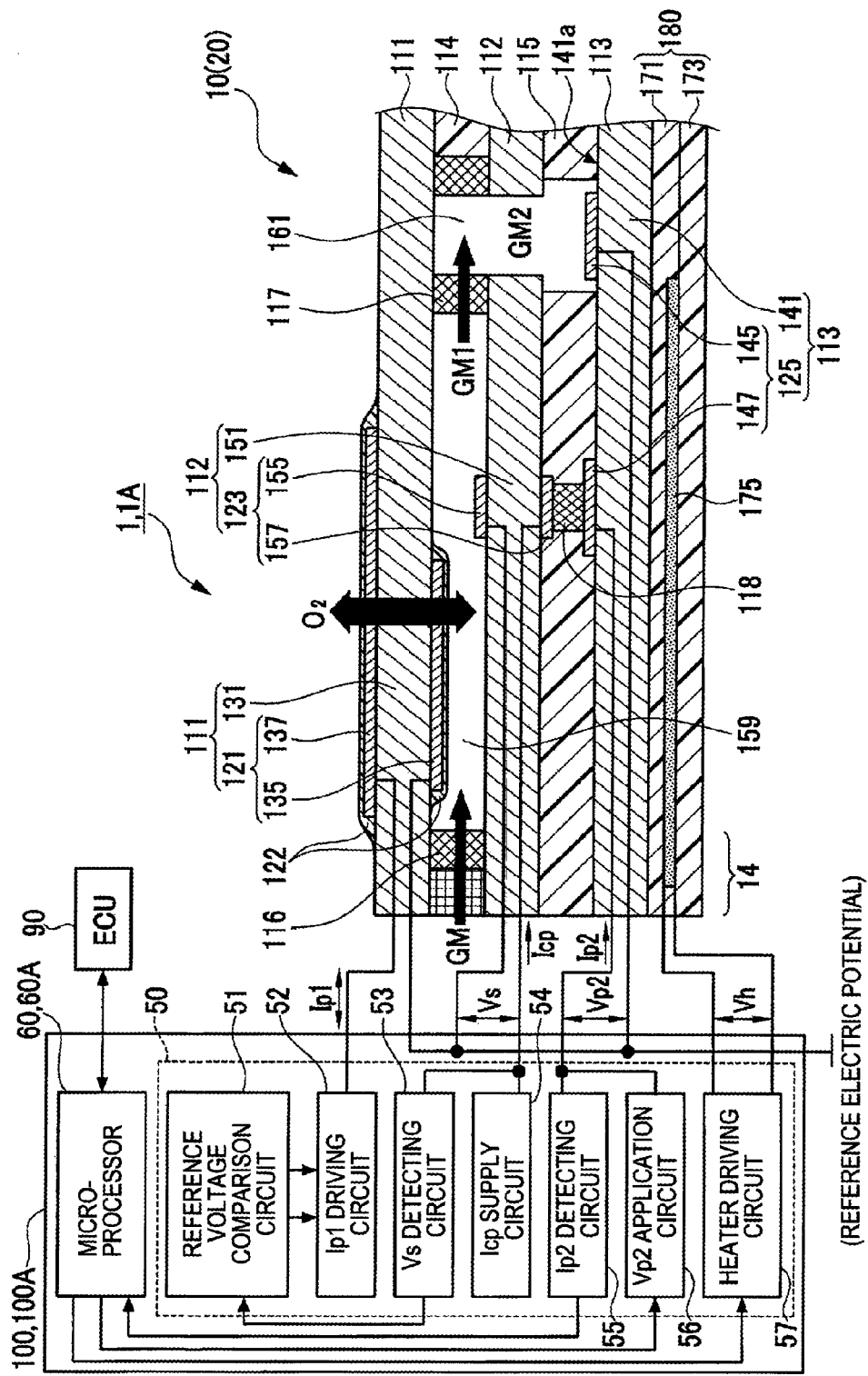
FIG. 1 schematically shows the configuration of a NOx sensor system (a gas sensor system) which includes a gas sensor control apparatus and a NOx sensor having a NOx sensor element according to Embodiments 1 and 2 of the invention.

Reference numerals used to identify various features in the drawings including the following.
60, 60A microprocessor
51 reference voltage comparison circuit
52 Ip1 driving circuit
53 Vs detecting circuit
54 Icp supply circuit
55 Ip2 detecting circuit
56 Vp2 application circuit
57 heater driving circuit

DETAILED DESCRIPTION OF THE PREFERRED EMBODIMENTS

Hereinafter, various embodiments of the invention will be described by reference to the drawings. However, the present invention should not be construed as being limited hereto.

Embodiment 1

FIG. 1 is an explanatory drawing which schematically shows the configuration of a NOx sensor system 1 (a gas sensor system) which includes a gas sensor control apparatus 100 and a NOx sensor 20 having a NOx sensor element 10 according to Embodiment 1.

The NOx sensor system 1 is installed in a vehicle (not shown) which includes an internal combustion engine (hereinafter, also referred to as an engine) to detect a NOx concentration in exhaust gas from the engine. This is done by controlling the NOx sensor element 10 (the NOx sensor 20) using the gas sensor control apparatus 100. In these constituent components, the NOx sensor 20 includes the NOx sensor element 10 and a main metallic member which accommodates the NOx sensor element 10 therein.

In FIG. 1, a left-hand side of the figure is referred to as a front end side, while a right-hand side of the figure is referred to as a rear end side of the NOx sensor element 10.

Firstly, the NOx sensor element 10 of the NOx sensor 20 will be described.

The NOx sensor element 10 has a construction in which a first pump cell 111, an oxygen concentration detecting cell 112 and a second pump cell 113 are laminated one on another via insulation layers 114, 115 which are formed mainly of alumina. A heater portion 180 is laminated on a side of the NOx sensor element 10 on which the second pump cell 113 is laminated.

The first pump cell 111 includes a first solid electrolyte layer 131 made of a solid electrolyte having oxygen ion transport properties formed mainly of zirconia and a pair of first porous electrodes 121 made of platinum which are disposed so as to sandwich the first solid electrolyte layer 131. The first porous electrode 121 includes a first pump first electrode 135 and a first pump second electrode 137, and surfaces of these electrodes are covered individually by a protection layer 122 which is made of a porous material.

In addition, the oxygen concentration detecting cell 112 includes a third solid electrolyte layer 151 made of a solid electrolyte formed mainly of zirconia and a pair of detecting porous electrodes 123 made of platinum which are disposed so as to sandwich the third solid electrolytic layer 151. Additionally, the detecting porous electrode 123 includes a detecting electrode 155 and a reference electrode 157.

Further, the second pump cell 113 includes a second solid electrolyte layer 141 made of a solid electrolyte material is formed mainly of zirconia and a pair of second porous electrodes 125 made of platinum which are disposed on a surface 141a of the second solid electrolyte layer 141 which faces the insulation layer 115. Additionally, the second porous electrode 125 includes a second pump first electrode 145 and a second pump second electrode 147.

A first measuring chamber 159 is defined in an interior of the NOx sensor element 10, and an external gas to be measured GM is introduced into the first measuring chamber 159 via first diffusion resistance element 116 which is disposed between the first pump cell 111 and the oxygen concentration detecting cell 112.

The first diffusion resistance element 116 is made of a porous material and is disposed along an introduction path for the gas to be measured GM. The first diffusion resistance element 116 extends from a front (a left-hand side in the figure) opening portion of the NOx sensor element 10 to the first measuring chamber 159 to limit an amount of gas to be measured GM which flows (passes) into the first measuring chamber 159 per unit time.

In addition, in the interior of the NOx sensor element 10, a second diffusion resistance element 117 made of a porous material is disposed in a position which corresponds to a rear end side (a right-hand side in the figure) of the first measuring chamber 159. Further, a second measuring chamber 161 is formed at a rear end side of the second diffusion resistance element 117, and a first chamber gas GM1 within the first measuring chamber 151 is introduced into the second measuring chamber 161 via the second diffusion resistance element 117. Additionally, the second measuring chamber 161 is formed so as to penetrate in the laminating direction of the insulation layers 114, 115 and the oxygen concentration detecting cell 112. The second pump first electrode 145 of the second pump cell 113 faces the second measuring chamber 161.

Further, in the interior of the NOx sensor element 10, a reference oxygen chamber 118 is defined between the third solid electrolyte layer 151 of the oxygen concentration detecting cell 112 and the second solid electrolyte layer 141 of the second pump cell 113. The reference oxygen chamber 118 is surrounded by the third solid electrolyte layer 151 of the oxygen concentration detecting cell 112, the second solid electrolyte layer 141 of the second pump cell 113 and the insulation layer 115. Additionally, the reference electrode 157 of the oxygen concentration detecting cell 112 and the second pump second electrode 147 of the second pump cell 113 are disposed so as to face the reference oxygen chamber 118.

The heater portion 180 is a laminate of sheet-like insulation layers 171, 173 made of an insulating ceramic such as alumina. Additionally, the heater portion 180 includes a heating pattern 175 made mainly of platinum which is provided between the insulation layers 171, 173.

Next, the gas sensor control apparatus 100 will be described.

The gas sensor control apparatus 100 includes mainly a microprocessor 60 and an electric circuit portion 50, and the electric circuit portion 50 is electrically connected to the NOx sensor element 10 of the NOx sensor 20. Additionally, the microprocessor 60 is connected to an ECU 90. In the gas sensor control apparatus 100 configured as described above, the microprocessor 60 drives and thereby controls the NOx sensor element 10 so as to detect a NOx concentration in exhaust gas according to a command from the ECU 90.

Additionally, the electric circuit portion 50 includes a reference voltage comparison circuit 51, an Ip1 driving circuit 52, a Vs detecting circuit 53, an Icp supply circuit 54, an Ip2 detecting circuit 55, a Vp2 application circuit 56 and a heater driving circuit 57.

The Icp supply circuit 54 supplies a minute self-generated current Icp between the detecting electrode 155 and the reference electrode 157 of the oxygen concentration detecting cell 112. By doing so, oxygen is drawn out from an interior of the first measuring chamber 159 into an interior of the reference oxygen chamber 118, whereby an atmosphere of a predetermined oxygen concentration can be set in the reference oxygen chamber 118.

The Vs detecting circuit 53 detects a concentration detecting voltage Vs between the detecting electrode 155 and the reference electrode 157 of the oxygen concentration detecting cell 112, and outputs the detected concentration detecting voltage to the reference voltage comparison circuit 51.

The reference voltage comparison circuit 51 compares the concentration detecting voltage Vs detected in the Vs detecting circuit 53 with a preset reference voltage (for example, 425 mV), and outputs the comparison result to the Ip1 driving circuit 52.

The Ip1 driving circuit 52 supplies a first pump current Ip1 between the first pump first electrode 135 and the first pump second electrode 137 of the first pump cell 111, and controls the magnitude and direction of the first pump current Ip1 so that the concentration detecting voltage Vs coincides with the reference voltage based on the result of the comparison made by the reference voltage comparison circuit 51. As a result, in the first pump cell 111, oxygen is drawn out from an interior of the first measuring chamber 159 to the outside of the NOx sensor element 10, or oxygen is drawn in from the outside of the NOx sensor element 10 into the interior of the first measuring chamber 159.

Thus, the first pump current Ip1 which flows to the first pump cell 111 is controlled so that the concentration detecting voltage Vs between the detecting electrode 155 and the reference electrode 157 of the oxygen concentration detecting cell 112 maintains the reference voltage, whereby the oxygen concentration of the first chamber gas GM1 in the interior of the first measuring chamber 159 is controlled to a predetermined concentration (a first concentration).

Then, the first chamber gas GM1 which is controlled to the first concentration is introduced into the second measuring chamber 161 via the porous second diffusion resistor element 117.

The Vp2 application circuit 56 applies a second pump voltage Vp2 between the second pump first electrode 145 and the second pump second electrode 147 of the second pump cell 113. This second pump voltage Vp2 is understood to be a predetermined detecting voltage Vp2a (in this embodiment, Vp2a=450 mV) in detecting a specific gas (NOx) concentration.

In this manner, NOx in the second chamber gas GM2 in an interior of the second measuring chamber 161 is dissociated by catalytic action of the second pump first electrode 145 of the second porous electrode 125 which makes up the second pump cell 113. Further, oxygen ion generated by the dissociation moves in the second solid electrolyte layer 141, whereby a second pump current Ip2 which corresponds to a specific gas (NOx) concentration flows between the second pump first electrode 145 and the second pump second electrode 147.

Namely, the second pump cell 113 dissociates the specific gas component (NOx) residing in the second chamber gas GM2 in the interior of the second measuring chamber 161, and draws out oxygen from the second measuring chamber 161 into the reference oxygen chamber 118.

Additionally, the Ip2 detecting circuit 55 detects a magnitude of the second pump current Ip2 which flows between the second pump first electrode 145 and the second pump second electrode 147.

The heater driving circuit 57 which applies voltage Vh to the heating pattern 175 is controlled by the microprocessor 60, to thereby control the energization of the heating pattern 175 of the heater portion 180 and cause the heater portion 180 to generate heat. By doing so, the first solid electrolyte layer 131 of the first pump cell 111, the third solid electrolyte layer 151 of the oxygen concentration detecting cell 112 and the second solid electrolyte layer 141 of the second pump cell 113 are heated to an activation temperature (for example, 750° C.).

In the above configuration, the NOx sensor element 10 is controlled by the gas sensor control apparatus 100, to thereby detect a NOx concentration in the exhaust gas from the magnitude of the second pump current Ip2.

However, since the response of the NOx sensor element 10 is delayed when the NOx sensor element 10 deteriorates as a result of use or the like, there is a concern that a required detecting performance cannot be met due to deterioration of the NOx sensor element 10. To address this problem, the gas sensor control apparatus 100 includes a means for determining a deterioration state (a deteriorated response) of the NOx sensor element 10 whose response is now delayed.

Specifically, in the gas sensor control apparatus 100 of Embodiment 1, the Vp2 application circuit 56 can switch the second pump voltage Vp2 from the detecting voltage Vp2a (=450 mV) for detecting the specific gas (NOx) concentration to a determination voltage Vp2b (in Embodiment 1, Vp2b=490 mV) which is higher than the detecting voltage Vp2a.

As described above, the second pump current Ip2 flows between the second pump first electrode 145 and the second pump second electrode 147 of the second pump cell 113 by setting the second pump voltage Vp2 to the detecting voltage Vp2a by the Vp2 application circuit 56.

Figure 2:
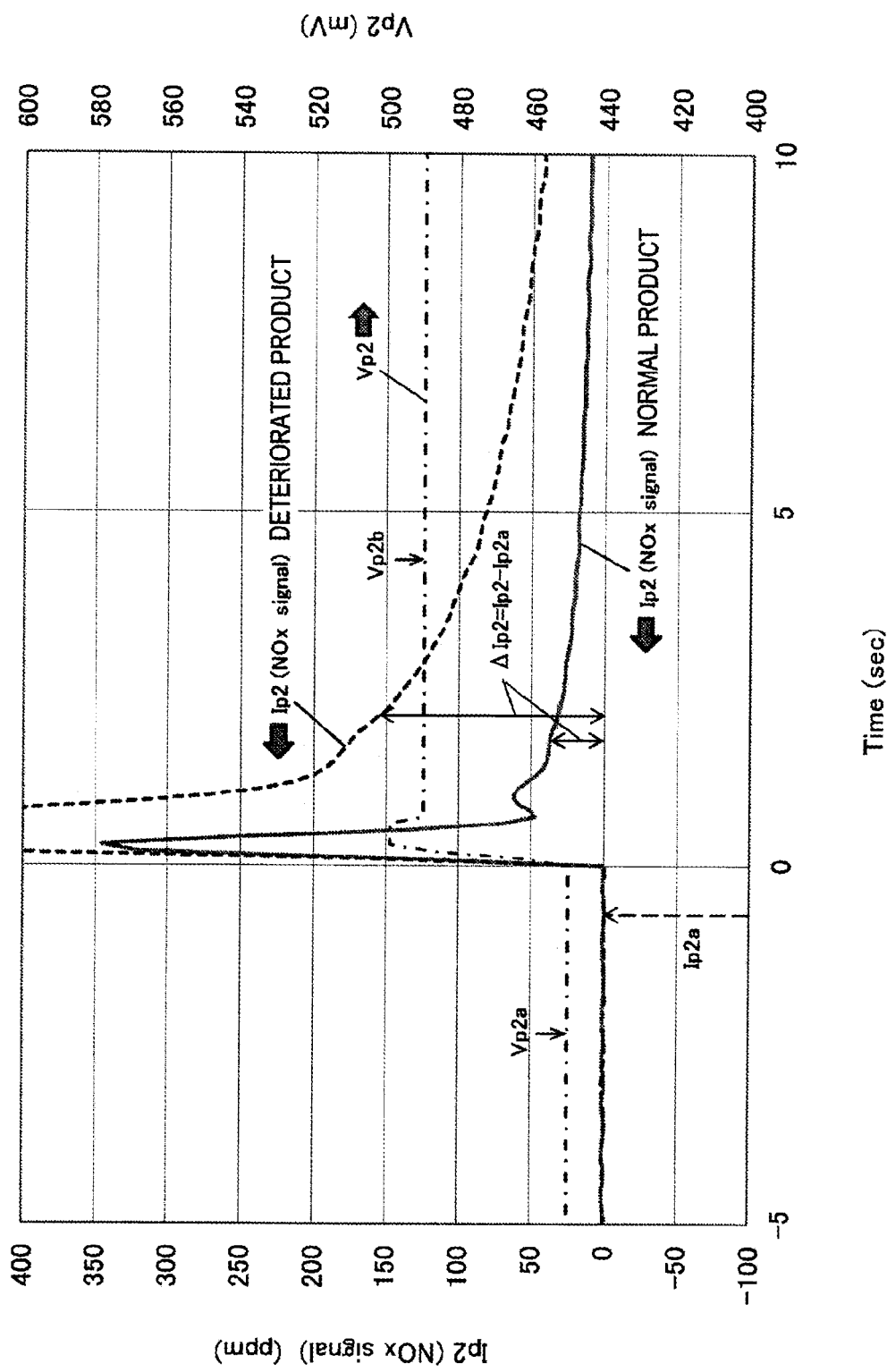
FIG. 2 shows a difference in transient response of a second pump current which is triggered by deterioration of the NOx sensor element.

Here, when the second pump voltage Vp2 is switched from the detecting voltage Vp2a (=450 mV) to the determination voltage Vp2b (=490 mV) which is higher than the detecting voltage Vp2a as indicated by a long and short alternate dash line in FIG. 2, a transient response is generated in which the second pump current Ip2 steeply rises immediately after the switching of the second pump voltage Vp2 and then begins to decline after passing its peak, as indicated by a solid line in FIG. 2.

However, the transient response of the second pump current Ip2 differs depending on the deterioration state of the NOx sensor element 10. Specifically, as seen from a comparison between a deteriorated product (deteriorated by a durability test) which is indicated by a broken line in FIG. 2 with a normal product (not previously subjected to a durability test) which is indicated by the solid line, a peak value of the second pump current Ip2 becomes higher as the NOx sensor element 10 further deteriorates. Additionally, in the deteriorated product, the second pump current Ip2 decreases at a slower rate once it begins to decline than in the normal product. Consequently, it is possible to determine whether or not the NOx sensor element 10 is deteriorated (i.e., whether or not the response is deteriorated), from the transient response of the second pump current Ip2.

In FIG. 2, an axis of ordinates on a left-hand side represents the magnitude (in ppm) of the second pump current Ip2 which is correlated to NOx concentration. Additionally, an axis of ordinates on a right-hand side represents a voltage value (in mV) of the second pump voltage Vp2, and an axis of abscissae represents passage (in sec) of time based on the switching timing of the second pump voltage Vp2. Additionally, in FIG. 2, the second pump currents Ip2 of both the normal product and the deteriorated product were measured under an environment where the NOx concentration was 0 ppm and after the switching of the second pump voltage Vp2. This also applies to FIGS. 3 and 6, which will be discussed below.

Hereinafter, a method of determining the deterioration state of the NOx sensor element 10 by the gas sensor control apparatus 100 of Embodiment 1 will be described schematically by reference to FIGS. 1 to 3.

In the gas sensor control apparatus 100 of Embodiment 1, the deterioration state of the NOx sensor element 10 is determined immediately after the engine is stopped by a command from the ECU 90.

When a determination process of the deterioration state of the NOx sensor element 10 starts, firstly, the second pump current Ip2a is measured by the Ip2 detecting circuit 55 and is stored as a pre-switching current Ip2a which results before the second pump voltage Vp2 is switched (refer to FIG. 2). Then, the second pump voltage Vp2 is switched from the detecting current Vp2a (=450 mV) to the determination voltage Vp2b (=490 mV) in a stepwise state by the Vp2 application circuit 56. By this switching, the second pump current Ip2 rises once from the pre-switching current Ip2a immediately after the switching of the second pump voltage Vp2, and then begins to decline after passing its peak and continues to decline during a decline period following thereafter.

Then, the second pump current Ip2 is sequentially measured by the Ip2 detecting circuit 55 to obtain a difference value $\Delta Ip2$ (=Ip2−Ip2a) between the second pump current Ip2 and the pre-switching current Ip2a (refer to FIG. 2). Then, as shown in FIG. 3, in the gas sensor control apparatus 100 of Embodiment 1, a timing (a threshold arrival timing tr) at which the difference value $\Delta Ip2$ becomes equal to or less than a predetermined threshold current value $\Delta Ipj$ (for example, 75 ppm or smaller in terms of NOx concentration) after passing its peak is detected to thereby measure a required time Tp elapsed from the switching of the second pump voltage Vp2 to the threshold arrival timing tr. In FIG. 3, in the case of the NOx sensor element 10 being normal (indicated by a solid line), the required time Tp (=Tp1) to the threshold arrival timing tr (=tr1) is short, whereas in the case of a deteriorated NOx sensor element 10 (indicated by a broken line), the required time Tp (=Tp2) to the threshold arrival timing tr (=tr2) is long.

Then, when the required time Tp is longer than a predetermined deterioration determination time length Tj (for example, Tj=3.0 seconds), a determination is made that the NOx sensor element 10 is deteriorated (the response thereof is deteriorated).

Next, in the gas sensor control apparatus 100 according to Embodiment 1, the operation of the microprocessor 60 which realizes the determination method described above will be described by reference to the flowcharts shown in FIGS. 4 and 5.

Figure 4:
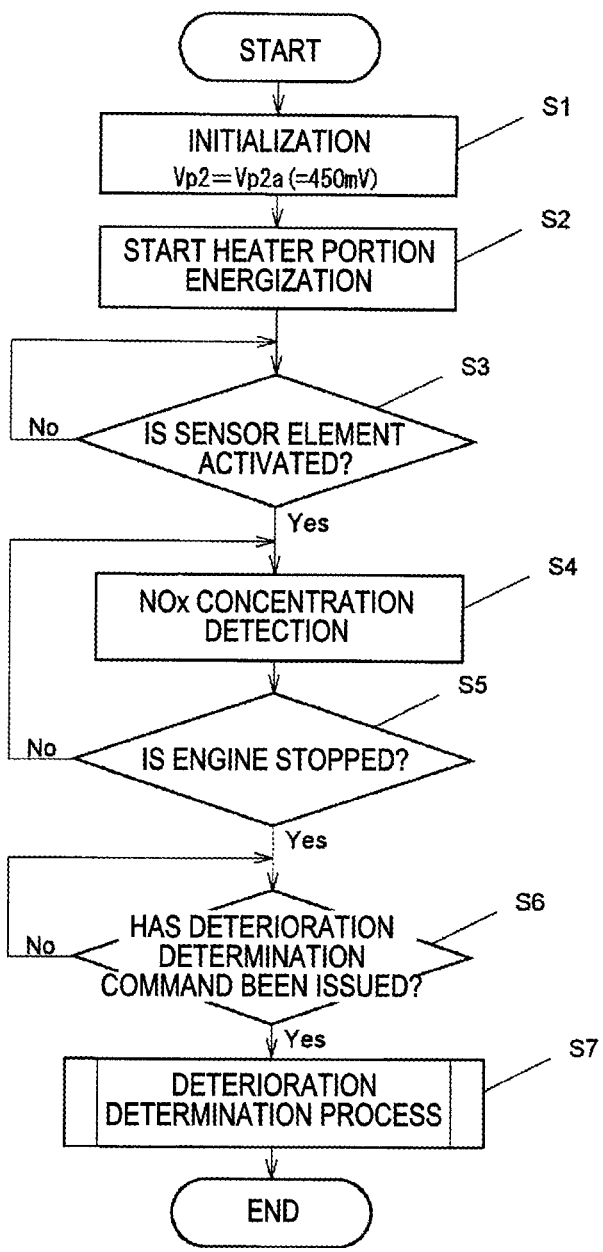
FIG. 4 is a flowchart which shows a processing operation of a microprocessor of the gas sensor control apparatus according to Embodiments 1 and 2.
Figure 5:
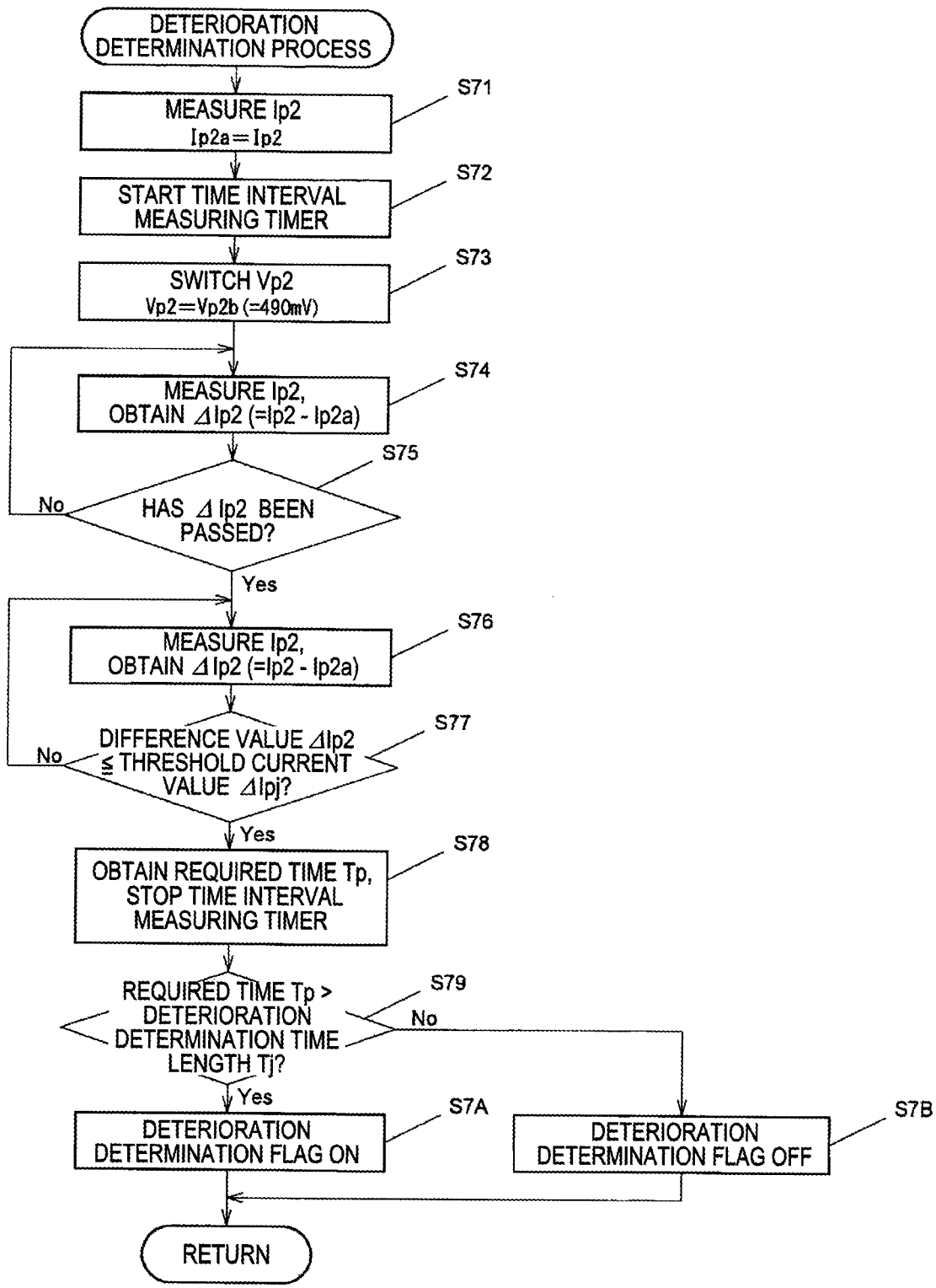
FIG. 5 is a flowchart which shows a deterioration determination routine according to Embodiment 1.

As shown in FIG. 4, when the engine is started and the microprocessor 60 of the gas sensor control apparatus 100 starts the process, firstly, various initializations are carried out in step S1, and in association with this, the second pump voltage Vp2 is set to the detecting voltage Vp2a (=450 mV) by the Vp2 application circuit 56.

Following this, in step S2, the heater circuit 180 begins to be energized by the heater driving circuit 57.

In step S3 which follows, a determination is made as to whether or not the NOx sensor element 10 is activated. If the NOx sensor element 10 has not yet been activated (No), this step S3 continues to wait for the NOx sensor element 10 to be activated. Then, when the NOx sensor element 10 is activated and the determination in step S3 is made as Yes, then, the operation flow proceeds to step S4.

In step S4, a NOx concentration is detected, and in step S5 which follows, information on whether or not the engine is stopped is obtained from the ECU 90. If the engine has not yet been stopped, a negative determination is made in step S5, whereby the detection of NOx concentration continues by repeating the operations in steps S4 and S5.

Then, when the engine is stopped and the determination in step 5 is made as Yes, the operation flow proceeds to step S6.

In step S6, a determination is made as to whether or not the ECU 90 has issued a determination that the NOx sensor element 10 is deteriorated. If a determination that NOx sensor element 10 is deteriorated and has not yet been issued from the ECU 90 (No), the operation in step S6 continues to wait for a determination as to deterioration of the NOx sensor element 10 to be issued from the ECU 90. Then, if the deterioration determination is issued from the ECU 90 (Yes), the operation flow proceeds to step S7. A deterioration determination process routine shown in FIG. 5 which starts from step S71 is then executed, whereafter the process by the microprocessor 60 is completed.

Next, the deterioration determination process routine shown in FIG. 5 will be described.

Firstly, in step S71, the second pump current Ip2 is measured by the Ip2 detecting circuit 55, and the measurement is stored as the pre-switching current Ip2a.

Following this, in step S72, a time interval measuring timer is started which measures the required time Tp by using a timer and counter incorporated in the microprocessor 60.

Then, in step S73 which follows, the second pump voltage Vp2 is switched to the determination voltage Vp2b (=490 mV) in a stepwise state by the Vp2 application circuit 56.

Next, in step S74, the second current Ip2 is measured by the Ip2 detecting circuit 55 to obtain a difference value ΔIp2 (=Ip2−Ip2a) between the second pump current Ip2 and the pre-switching current Ip2a.

Then, in step S75 which follows, a determination is made that the difference value ΔIp2 has passed its peak and the process routine waits for the difference value ΔIp2 to pass its peak by repeating the operations in steps S74 and S75.

Then, when the difference value ΔIp2 passes its peak, an affirmative determination is made in step S75, and the operation flow proceeds to step S76.

In step S76, as with step S74, the second current Ip2 is measured by the Ip2 detecting circuit 55 to obtain a difference value ΔIp2 between the second pump current Ip2 and the pre-switching current Ip2a.

Then, in step S77 which follows, a determination is made as to whether or not the difference value ΔIp2 is equal to or smaller than the threshold current value ΔIpj (refer to FIG. 3), and the process routine waits for the difference value ΔIp2 to become equal to or smaller than the threshold current value ΔIpj by repeating the operations in steps S76 and S77.

Then, when the difference value ΔIp2 becomes equal to or smaller than the threshold current value ΔIpj, the determination is made as Yes in step S77, and the operation flow proceeds to step S78 (the threshold arrival timing tr).

In step S78, a count value of the time interval measuring timer which was started in step S72 is obtained to obtain a required time Tp which has elapsed from the switching of the second pump voltage Vp2 in step S73 to the step S78 (the threshold arrival timing tr), after which the time interval measuring timer is stopped.

Figure 3:
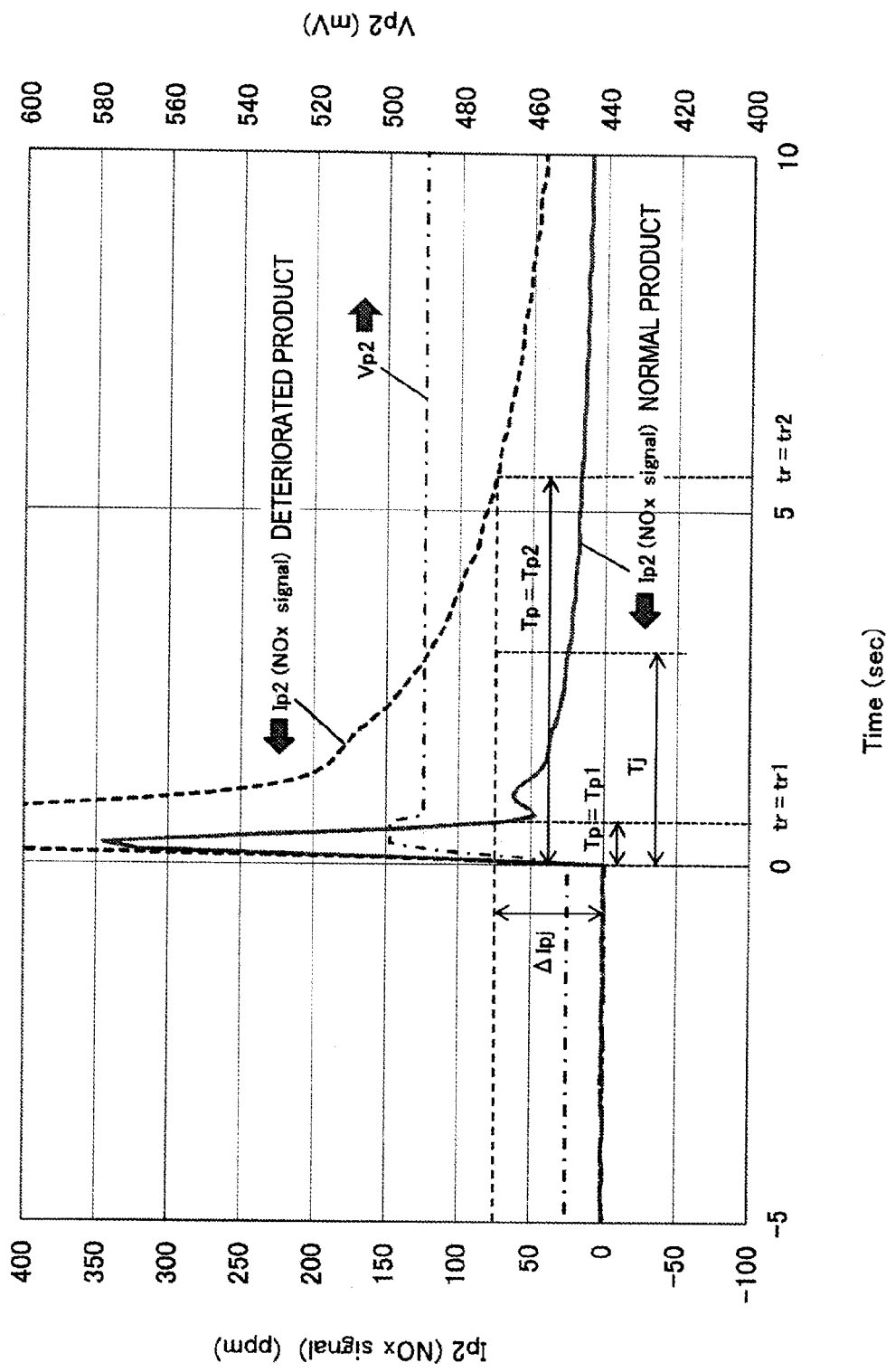
FIG. 3 illustrates a method of determining the deterioration state of the NOx sensor element according to Embodiment 1.

Then, in step S79 which follows, a determination is made as to whether or not the obtained required time Tp is longer than the predetermined deterioration determination time length Tj (refer to FIG. 3). If the required time Tp is longer than the deterioration determination time length Tj, the determination is made as Yes in step S79. Then, the operation flow proceeds to step S7A, where it is determined that the NOx sensor element 10 is deteriorated, and a deterioration determination flag is turned on (set). On the other hand, if the determination is made as No in step S79, the operation flow proceeds to step S7B, where a determination is made that the NOx sensor element 10 is not deteriorated, and the deterioration determination flag is turned off (reset).

Then, the deterioration determination process routine is completed after step S7A or step S7B.

If the deterioration determination flag is on (set) in step S7A, the microprocessor 60 separately informs the ECU 90 that the NOx sensor element 10 is deteriorated. Then, the ECU 90 executes a predetermined warning operation in which the ECU notifies the user that the NOx sensor element 10 is deteriorated and urges the user to replace the deteriorated NOx sensor element 10 with a new one.

In Embodiment 1, the NOx sensor element 10 corresponds to a gas sensor element and the NOx sensor 20 corresponds to a gas sensor of the invention. Additionally, the second pump cell 113 corresponds to a second chamber pump cell, and the pair of second porous electrodes 125 which includes the second pump first electrode 145 and the second pump second electrode 147 corresponds to a pair of electrodes of the invention.

In addition, the second pump voltage Vp2 corresponds to a second chamber pump voltage and the second pump current Ip2 corresponds to a concentration-representing current of the invention.

Additionally, the reference voltage comparison circuit 51, the Ip1 drive circuit 52, and the Vs detecting circuit 53 corresponds to a first chamber control unit and the Vp2 application circuit 56 corresponds to a second chamber control unit of the invention.

Additionally, the Ip2 detecting circuit 55 corresponds to a current detecting unit, and the Vp2 application circuit 56 and the microprocessor 60 which executes the operation in step S73 correspond to a voltage changing unit and a voltage switching unit, respectively.

In addition, the microprocessor 60 which executes the deterioration determination process routine in step S7 (from step S71 downward) corresponds to a deterioration determination unit of the invention.

Further, the microprocessor 60 which executes step S76 corresponds to a difference value obtaining unit, and the microprocessor 60 which executes step S72 and steps S76 to S78 corresponds to a timing detecting unit of the invention. Additionally, the threshold current value ΔIpj corresponds to a first threshold current value of the invention. Additionally, the microprocessor 60 which executes steps S79, S7A, S7B corresponds to a first determination unit of the invention.

Thus, the gas sensor control apparatus 100 of Embodiment 1 includes the voltage changing unit (the Vp2 application circuit 56, step S73) which changes the second pump voltage Vp2 (the second chamber pump voltage) that is applied between the second pump first electrode 145 and the second pump second electrode 147 of the second pump cell 113 and the deterioration determination unit (step S7 (step S71 downward)) which determines the deterioration state of the NOx sensor element 10 from the transient response which is generated in association with a change in the second pump voltage Vp2 (the second chamber pump voltage).

In the transient response of the second pump current Ip2 which is generated by changing the second pump voltage Vp2, as shown in FIGS. 2 and 3, the peak value of the second pump current Ip2 increases as the NOx sensor element 10 further deteriorates, and the second pump current Ip2 decreases at a slower rate once it begins to decline after passing its peak. Consequently, in the gas sensor control apparatus 100, the deterioration of the NOx sensor element 10 (the deterioration in response) can be appropriately determined from the transient response of the second pump current Ip2 by the deterioration determination unit (step S7 (step S71 downward)).

In addition, the NOx sensor system 1 which can appropriately determine the deterioration state of the NOx sensor element 10 (the deterioration in response) may comprise the gas sensor control apparatus 100 and the NOx sensor 20 including the NOx sensor element 10 according to Embodiment 1.

Further, in the gas sensor control apparatus 100 of Embodiment 1, the second pump voltage Vp2 (the second chamber pump voltage) is switched from the detecting voltage Vp2a (=450 mV) to the determination voltage Vp2b (=490 mV) by the voltage switching unit (the Vp2 application circuit 56, step S73) as the voltage changing unit. In addition, the deterioration state of the NOx sensor element 10 is determined by the deterioration determination unit (step S7 (step S71 downward)) based on the change in the second pump current Ip2 of the transient response of the second pump current Ip2 (the concentration-representing current) which is generated by the switching of the second pump voltage Vp2.

As shown in FIGS. 2 and 3, when the second pump voltage Vp2 is switched from the detecting voltage Vp2a to the determination voltage Vp2b which is higher than the detecting voltage Vp2a, a transient response is generated in which the second pump current Ip2 steeply rises immediately after the second pump voltage Vp2 is so switched and then begins to decline after passing its peak. Additionally, in this transient response, the peak value of the second pump current Ip2 increases as the NOx sensor element 10 further deteriorates, and the second pump current Ip2 decreases at a slower rate once it begins to decline after passing its peak. Consequently, the change in the second pump current Ip2 which is generated in the decline period which follows the switching of the second pump voltage Vp2 reflects the deterioration state of the NOx sensor element 10. Because of this, in the gas sensor control apparatus 100 of Embodiment 1, the deterioration state of the NOx sensor element 10 can be appropriately determined based on the change in the second pump current Ip2 occurring in the decline period.

Further, in the gas sensor control apparatus 100 of Embodiment 1, the deterioration determination unit includes the timing detecting unit (steps S72, S76 to 78) and the first determination unit (steps S79, S7A, S7B), and determines the deterioration state of the NOx sensor element 10 based on the threshold arrival timing tr at which the difference value ΔIp2 (=Ip2−Ip2a) between the second pump current Ip2 and the pre-switching current Ip2a becomes equal to or smaller than the predetermined threshold current value ΔIpj.

By doing so, the change in the second pump current Ip2 (the concentration-dependent current) which occurs in the decline period as a result of deterioration of the NOx sensor element 10 is obtained as the threshold arrival timing tr, whereby the deterioration state of the NOx sensor element 10 can be appropriately determined.

Further, in the gas sensor control apparatus 100 of Embodiment 1, the time elapsed from the switching of the second pump voltage Vp2 (step S73) to the threshold arrival timing tr (step S78) is obtained as the required time Tp, whereby it is possible to easily and appropriately determine whether or not the NOx sensor element 10 has deteriorated by comparing the required time Tp with the deterioration determination time length Tj.

Embodiment 2

Next, a second embodiment of the invention will be described by reference to the drawings. A gas sensor control apparatus 100A according to Embodiment 2 has almost the same configuration as that of the gas sensor control apparatus 100 of Embodiment 1 and includes mainly, as shown in FIG. 1, a microprocessor 60A and an electric circuit portion 50. Additionally, the gas sensor control apparatus 100A and a NOx sensor 20 which has a NOx sensor element 10 make up a NOx sensor system 1A (a gas sensor system). In addition, the electric circuit portion 50 is electrically connected with the NOx sensor element 10 of the NOx sensor 20, and the microprocessor 60A is connected to an ECU 90.

By adopting this configuration, in the gas sensor control apparatus 100A, the microprocessor 60A drives and controls the NOx sensor element 10 to detect a NOx concentration in the exhaust gas.

Embodiment 2 partially differs from Embodiment 1 in the method for determining the deterioration state of the NOx sensor element 10, and a deterioration determination process routine executed by the microprocessor 60A differs from that of Embodiment 1. However, in the NOx sensor system 1A, the configurations of an electric circuit portion 50 and the NOx sensor element 10 of the NOx sensor 20 of the gas sensor control apparatus 100A and a method for detecting a NOx concentration are the same as those of Embodiment 1, and therefore, a description thereof will be omitted here.

Hereinafter, a method for determining the deterioration state of the NOx sensor element 10 by the gas sensor control apparatus 100A of Embodiment 2 will be described schematically by reference to FIGS. 1, 2 and 6.

Also, in the gas sensor control apparatus 100A of Embodiment 2, as with the gas sensor control apparatus 100 of Embodiment 1, a Vp2 application circuit 56 of the electric circuit portion 50 can switch a second pump voltage Vp2 from a detecting voltage Vp2a (=450 mV) to a determination voltage Vp2b (=490 mV) which is higher than the detecting voltage Vp2a.

When the ECU 90 issues a command to initiate a determination process of determining the deterioration state of the NOx sensor element 10 immediately after an engine is stopped, as in the case with Embodiment 1, the Ip2 detecting circuit 55 measures a second pump current Ip2 and stores the measured second pump current Ip2 as a pre-switching current Ip2a which results before the second pump voltage Vp2 is switched (refer to FIG. 2). Then, the Vp2 application circuit 56 switches the second pump voltage Vp2 from the detecting voltage Vp2a (=450 mV) to the determination voltage Vp2b (=490 mV) in a stepwise state.

Then, the second pump current Ip2 shifts to begin a decline after passing its peak. In the gas sensor control apparatus 100A of Embodiment 2, differing from Embodiment 1, when the Vp2 application circuit 56 switches the second pump voltage Vp2, a predetermined deterioration determination time tmj (for example, tmj=3.0 seconds) is measured from that switch point as an originating point, and the routine waits for the deterioration determination time tmj to be reached (refer to FIG. 6). Note that this deterioration determination time tmj is set to any point during a decline period which follows the decline of the second pump current Ip2.

Figure 6:
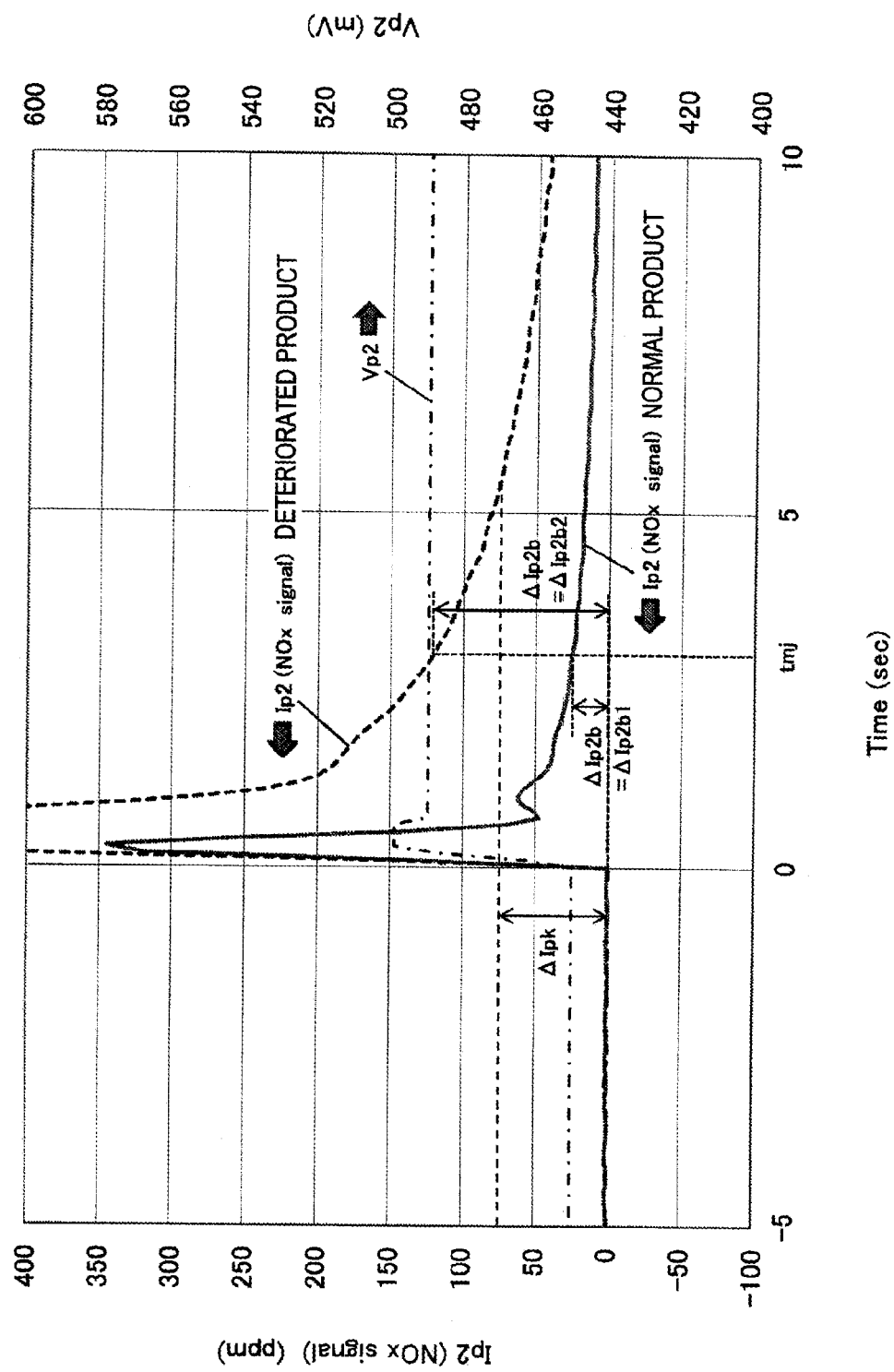
FIG. 6 illustrates a method of determining the deterioration of a NOx sensor element according to Embodiment 2.

Then, when the deterioration determination time tmj arrives, a determination difference value ΔIp2b (=Ip2−Ip2a) is obtained which is a difference between the second pump current Ip2 at the deterioration determination time tmj and the pre-switching current Ip2a (refer to FIG. 6). As shown in FIG. 6, in the event that the NOx sensor element 10 is normal (indicated by a solid line), the determination difference value ΔIp2b assumes a small value (ΔIp2b=ΔIp2b1), whereas in the event that the NOx sensor element 10 is deteriorated (indicated by a broken line), the determination difference value ΔIp2b assumes a large value (ΔIp2b=ΔIp2b2).

In addition, in the event that the determination difference value ΔIp2b is larger than a predetermined threshold current value ΔIpk (for example, 75 ppm in terms of NOx concentration), a determination is made that the NOx sensor element 10 is deteriorated.

Figure 7:
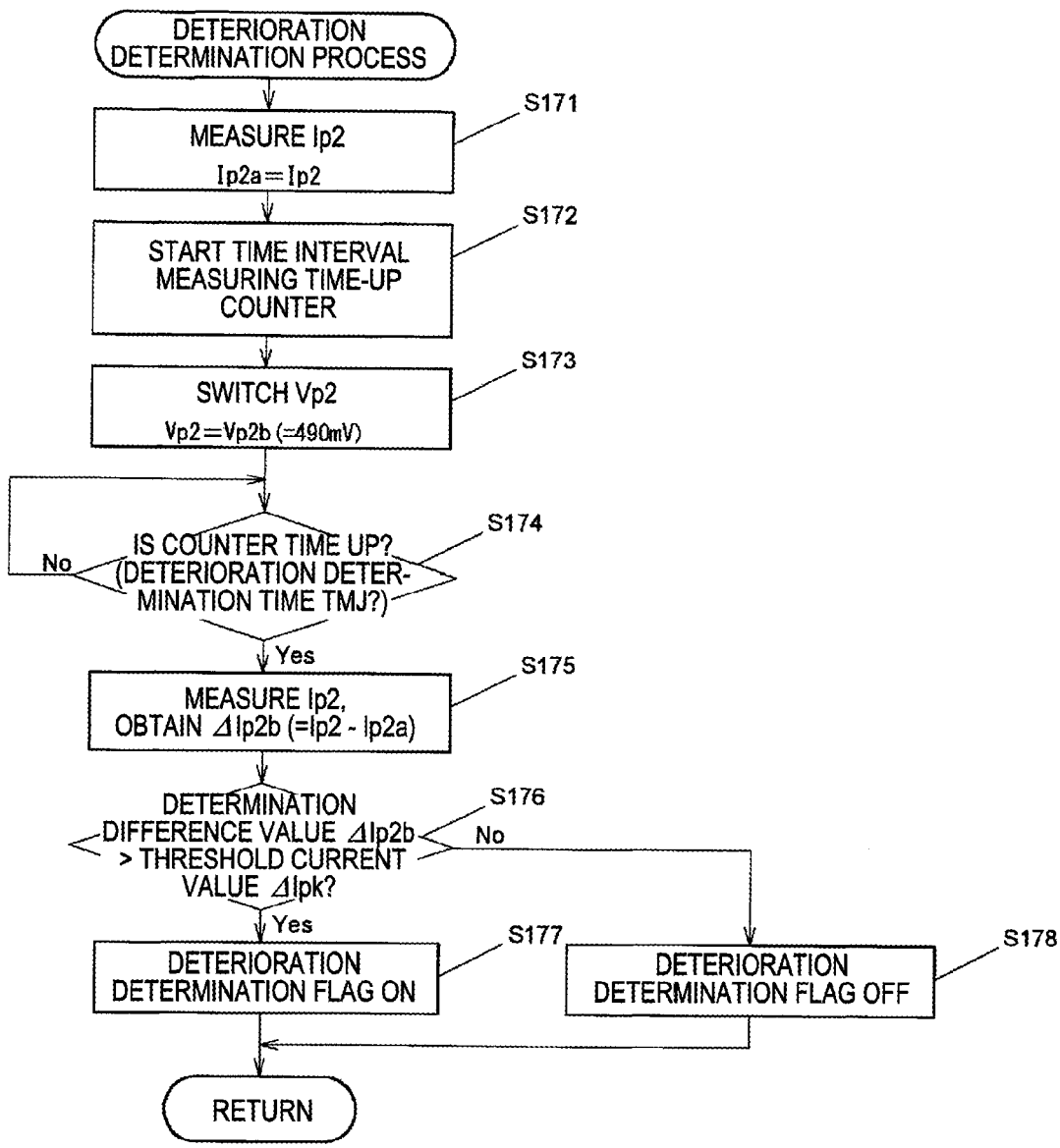
FIG. 7 is a flowchart which shows a deterioration determination routine according to Embodiment 2.

Next, in the gas sensor control apparatus 100A according to Embodiment 2, the operation of the microprocessor 60A for realizing the above determination method will be described by reference to the flowcharts shown in FIGS. 4 and 7. In the operation of the microprocessor 60A, an operation shown in FIG. 4 is the same as that of Embodiment 1, and when the ECU 90 issues a determination that the NOx sensor element 10 is deteriorated, the operation flow proceeds to step S7 in FIG. 4, where a deterioration determination process routine described from step S171 shown in FIG. 7 downward will be executed.

Hereinafter, the description of what is illustrated in FIG. 4 is omitted, and the deterioration determination process routine shown in FIG. 7 will be described.

Firstly, in step S171, the Ip2 detecting circuit 55 measures a second pump current Ip2 and stores it as the pre-switching current Ip2a.

Following this, in step S172, a time interval measuring time-up counter is started to measure the predetermined deterioration determination time tmj (=3.0 seconds) by the use of a timer and counter incorporated in the microprocessor 60A.

Then, in step S173 which follows, the Vp2 application circuit 56 switches the second pump voltage Vp2 to the determination voltage Vp2b (=490 mV) in a stepwise state.

Following this, in step S174, the process routine verifies whether or not the counting time of the time interval measuring time-up counter which was started in step S172 has expired. If the counting time has not yet expired (No), step S174 continues. By doing so, the process routine waits for the deterioration determination time tmj to arrive.

Then, when the deterioration determination time tmj arrives and the counting time of the time interval measuring time-up counter has expired, an affirmative determination is made in step S174, and the operation flow proceeds to step S175.

In step S175, the Ip2 detecting circuit 55 measures the second pump current Ip2 and obtains a determination difference value ΔIp2b (=ΔIp2−ΔIp2a) which is a difference value between the measured second pump current Ip2 and the pre-switching current Ip2a.

Then, in step S176 which follows, the process routine determines whether or not the determination difference value ΔIp2b is larger than a predetermined threshold current value ΔIpk (refer to FIG. 6). If the determination difference value ΔIp2b is larger than the threshold current value ΔIpk, an affirmative determination is made in step S176, and the operation flow proceeds to step S177, where the process routine determines that the NOx sensor element 10 is deteriorated, and a deterioration determination flag is turned on (set). On the other hand, if a negative determination is made in step S176, then, the operation flow proceeds to step S178, where the process routine determines that the NOx sensor element 10 is not deteriorated, and the deterioration determination flag is turned off (reset).

Then, the deterioration determination process routine is completed after step S177 or step S178.

As in the case with Embodiment 1, in the event that the deterioration determination flag is turned on (set) in step S177, the microprocessor 60A separately notifies the ECU 90 that the NOx sensor 10 is deteriorated. Then, the ECU 90 executes a predetermined warning process in which the user is urged to replace the deteriorated NOx sensor element 10 with a new one.

In Embodiment 2, the Vp2 application circuit 56 and the microprocessor 60A which executes step S173 correspond to the voltage changing unit and the voltage switching unit of the invention.

In addition, the microprocessor 60A which executes the deterioration determination process routine in step S7 (step S171 downward) corresponds to the deterioration determination unit of the invention.

Further, the microprocessor 60A which executes step S175 corresponds to the determination difference value obtaining unit of the invention. In addition, the threshold current value ΔIpk corresponds to a second threshold current value, and the microprocessor 60A which executes steps S176, S177, S178 corresponds to a second determination unit of the invention.

Thus, as described above, in the gas sensor apparatus 100A of Embodiment 2, it is possible to appropriately determine the deterioration state of the NOx sensor element 10 (the deterioration in response) based on the change in the second pump current Ip2 which occurs in the decline period by the deterioration determination unit (step S7 (S171 downward)) and the voltage switching unit (the Vp2 application circuit 56, step S173), as in Embodiment 1.

Additionally, it is possible to provide a gas sensor system which can appropriately determine the deterioration state of the NOx sensor element 10 (the deterioration in response) which system comprises the gas sensor control apparatus 100A and the NOx sensor system 1A including the NOx sensor 20 having the NOx sensor system according to Embodiment 2.

Further, in the gas sensor control apparatus 100A of Embodiment 2, the deterioration determination unit includes the determination difference value obtaining unit (step S175) and the second determination unit (steps S176, S177 S178) and determines the deterioration state of the NOx sensor element 10 based on the determination difference value ΔIp2b (=ΔIp2−ΔIp2a) which is the difference value between the second pump current Ip2 and the pre-switching current Ip2a at the predetermined deterioration determination time tmj during the decline period.

By doing so, it is possible to appropriately determine the deterioration state of the NOx sensor 10 by obtaining the change in the second pump current Ip2 during the decline period that occurs as a result of the deterioration of the NOx sensor element 10 as a change in the determination difference value ΔIp2b. In addition, since the time required for the deterioration determination is determined by the predetermined deterioration determination time tmj, even though the decline of the second pump current Ip2 becomes more gradual with progressing deterioration of the NOx sensor element 10, there is no situation in which it takes a long time to make a determination that the NOx sensor element 10 has deteriorated.

Further, in the gas sensor control apparatus 100A of Embodiment 2, it is possible to determine whether or not the NOx sensor element 10 is deteriorated simply and appropriately by comparing the determination difference value ΔIp2b with the predetermined threshold current value ΔIpk (the second threshold current value).

Thus, while the gas sensor control apparatus and the gas sensor system of the invention have been described based on the gas sensor control apparatuses 100, 100A and the NOx sensor systems 1, 1A of Embodiments 1, 2, the invention is not limited thereto. Namely, the invention can be carried out while being modified as required without departing from the spirit and scope of the claims appended hereto.

For example, in Embodiments 1, 2, the ECU 90 issues a command to determine the deterioration state of the NOx sensor element 10 immediately after the engine is stopped. Because of this, nothing is mentioned as to the fact that the Vp2 application circuit 56 switches the second pump voltage Vp2 from the detecting voltage Vp2a to the determination voltage Vp2b, after which the second pump voltage Vp2 is returned to the detecting voltage Vp2a to continue detecting the NOx concentration.

However, the deterioration determination may be made during an idling-stop or fuel-cut operation, and as this occurs, in order to resume the NOx concentration detection, the second pump voltage Vp2 is desirably returned to the detecting voltage Vp2a after the deterioration determination is made.

In addition, in Embodiments 1, 2, while the ECU 90 issues the command to determine the deterioration state of the NOx sensor element 10 immediately after the engine is stopped, the gas sensor control apparatuses 100, 100A may autonomously start the deterioration determination process without being instructed by the ECU 90.

Additionally, in Embodiments 1, 2, while each deterioration determination of the NOx sensor element 10 is executed after the engine is stopped by waiting for a command to be issued from the ECU 90, the deterioration determination of the NOx sensor element 10 may be arranged to occur at a predetermined cycle or every specific period of time such as once in 10 cyclic operations or once a month.

In addition, in Embodiments 1, 2, the deterioration of the NOx sensor element 10 is determined based on the change during the decline period beginning after the second pump current Ip2 shifts to start the decline after passing its peak. However, in place of this, the deterioration determination of the NOx sensor element 10 may be executed based on the peak value of the second current Ip2. Additionally, the deterioration determination may be executed based on both the peak value and the change in the decline period.

In addition, as the deterioration determination method during the decline period, in addition to those in Embodiments 1, 2, a method may be adopted in which a time constant of the second pump current Ip2 during the decline period is obtained or a function parameter of a curve matching the decline is obtained so that the deterioration determination is made based on the time constant or the function parameter so obtained.

In addition, in Embodiments 1, 2, while the second pump voltage Vp2 is switched from the detecting voltage Vp2a to the determination voltage Vp2b which is higher than the detecting voltage Vp2a in the stepwise state, the deterioration of the NOx sensor element 10 may be determined by obtaining a transient response of the second pump current by causing the second pump voltage Vp2 to change from the detecting voltage Vp2a to the determination voltage Vp2b in a ramp manner.

This application is based on Japanese Patent Application No. 2013-036939, filed Feb. 27, 2013, incorporated herein by reference in its entirety.

What is claimed is:

1. A gas sensor control apparatus for controlling a gas sensor element, the gas sensor element including: a first measuring chamber into which an external gas to be measured is introduced and a second measuring chamber in communication with the first measuring chamber and into which a first chamber gas in an interior of the first measuring chamber is introduced, the first measuring chamber and the second measuring chamber being formed in an interior of the gas sensor element; a second chamber pump cell made of a solid electrolyte; and a pair of electrodes which are provided on the second chamber pump cell and which are disposed inside and outside the second measuring chamber, the gas sensor control apparatus comprising:

first chamber control unit for controlling an oxygen concentration of the first chamber gas in the interior of the first measuring chamber to a first concentration;

second chamber control unit for applying a second chamber pump voltage and dissociating an oxygen-containing specific gas, which is contained in a second chamber gas in an interior of the second measuring chamber, between the pair of electrodes, so as to cause a concentration-dependent current, which corresponds to a concentration of the oxygen-containing specific gas in the second chamber gas in the interior of the second measuring chamber, to flow between the pair of electrodes;

current detecting unit for detecting a magnitude of the concentration-dependent current which flows between the pair of electrodes;

voltage changing unit for changing the second chamber pump voltage; and deterioration determination unit for determining the deterioration state of the gas sensor element based on a transient response of the concentration-dependent current which is generated in association with a change in the second chamber pump voltage, wherein the voltage changing unit includes voltage switching unit for switching, in a stepwise state, the second chamber pump voltage from a detecting voltage for detecting a specific gas concentration to a determination voltage which is higher than the detecting voltage, and wherein the deterioration determination unit determines the deterioration state of the gas sensor element based on, as the transient response of the concentration-dependent current which is generated by the switching of the second chamber pump voltage by the voltage switching unit, a change in the concentration-dependent current during a decline period, which is a period after the concentration-dependent current rises to its peak from a pre-switching current before the switching of the second chamber pump voltage and then declines.

2. The gas sensor control apparatus as claimed in claim 1, wherein the deterioration determination unit includes:

timing detecting unit for detecting a threshold arrival timing at which a difference value between the concentration-dependent current and the pre-switching current becomes equal to or smaller than a predetermined first threshold current value during the decline period; and first determination unit for determining the deterioration state of the gas sensor element based on the threshold arrival timing.

3. The gas sensor control apparatus as claimed in claim 2, wherein the first determination unit determines that the gas sensor element is deteriorated when a required time spent from the switching of the second chamber pump voltage to the threshold arrival timing is longer than a predetermined deterioration determination time length.

4. The gas sensor control apparatus as claimed in claim 1, wherein the deterioration determination unit includes:
   determination difference value obtaining unit for obtaining a determination difference value, which is a difference value between the concentration-dependent current at a predetermined deterioration determination time during the decline period and the pre-switching current; and
   second determination unit for determining the deterioration state of the gas sensor element based on the determination difference value.

5. The gas sensor control apparatus as claimed in claim 4, wherein the second determination unit determines that the gas sensor element is deteriorated when the determination difference value is larger than a predetermined second threshold current value.

6. A gas sensor system comprising:
the gas sensor control apparatus as claimed in claim 1; and
a gas sensor including the gas sensor element.

* * * * *